(12) United States Patent
Frenkel

(10) Patent No.: US 8,334,409 B2
(45) Date of Patent: Dec. 18, 2012

(54) PROCESS FOR PURIFYING RASAGILINE BASE

(75) Inventor: Anton Frenkel, Netanya (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 672 days.

(21) Appl. No.: 12/456,642

(22) Filed: Jun. 19, 2009

(65) Prior Publication Data

US 2010/0010095 A1  Jan. 14, 2010

Related U.S. Application Data

(60) Provisional application No. 61/132,512, filed on Jun. 19, 2008.

(51) Int. Cl.
*C07C 211/00* (2006.01)
(52) U.S. Cl. ........................................................ 564/428
(58) Field of Classification Search .................. None
See application file for complete search history.

(56) References Cited

U.S. PATENT DOCUMENTS

| | | |
|---|---|---|
| 4,529,811 A | 7/1985 | Hill et al. |
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,271,263 B1 | 8/2001 | Sklarz et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,635,667 B2 | 10/2003 | Thomas |
| 6,956,060 B2 | 10/2005 | Youdim et al. |
| 7,309,497 B2 | 12/2007 | Rimpler et al. |
| 7,396,860 B2 | 7/2008 | Blaugrund et al. |

(Continued)

FOREIGN PATENT DOCUMENTS

WO  WO 02/068376  9/2002

(Continued)

OTHER PUBLICATIONS

Mallory, F. J. Chem. Educ., 1962, 39(5), p. 261.*

(Continued)

*Primary Examiner* — Johann Richter
*Assistant Examiner* — Clinton Brooks
(74) *Attorney, Agent, or Firm* — John P. White; Gary J. Gershik; Cooper & Dunham LLP

(57) ABSTRACT

Disclosed is crystalline R(+)-N-propargyl-1-aminoindan and racemic N-propargyl-1-aminoindan characterized by colorless crystals a pharmaceutical composition comprising the same, and the process for the manufacture and the validation thereof. Also disclosed is pure liquid R(+)-N-propargyl-1-aminoindan and a pharmaceutical composition comprising the same, and the process for the manufacture thereof.

20 Claims, 3 Drawing Sheets

Figure 1. Effect of pressure on evaporation/sublimation rate of liquid Rasagiline base at 60C

U.S. PATENT DOCUMENTS

| | | | |
|---|---|---|---|
| 7,491,847 B2 | 2/2009 | Frenkel | |
| 7,547,806 B2 | 6/2009 | Frenkel et al. | |
| 7,572,834 B1 | 8/2009 | Sterling et al. | |
| 7,598,420 B1 | 10/2009 | Sterling et al. | |
| 7,618,041 B1 | 11/2009 | Sterling et al. | |
| 7,750,051 B2 * | 7/2010 | Frenkel et al. | 514/647 |
| 7,815,942 B2 | 10/2010 | Peskin | |
| 7,855,233 B2 | 12/2010 | Frenkel et al. | |
| 7,968,749 B2 | 6/2011 | Frenkel et al. | |
| 8,080,584 B2 | 12/2011 | Safadi et al. | |
| 2003/0014879 A1 | 1/2003 | Horigame | |
| 2003/0087814 A1 | 5/2003 | Lederman | |
| 2003/0180332 A1 | 9/2003 | Rimpler et al. | |
| 2004/0157784 A1 | 8/2004 | Chopdekar et al. | |
| 2005/0019399 A1 | 1/2005 | Fischer et al. | |
| 2006/0018957 A1 | 1/2006 | Lerner et al. | |
| 2006/0094783 A1 | 5/2006 | Youdim et al. | |
| 2006/0142374 A1 | 6/2006 | Tsuru et al. | |
| 2006/0188581 A1 | 8/2006 | Peskin | |
| 2007/0100001 A1 | 5/2007 | Youdim et al. | |
| 2007/0116729 A1 | 5/2007 | Palepu | |
| 2007/0232700 A1 | 10/2007 | Blaugrund et al. | |
| 2008/0038833 A1 | 2/2008 | Popp | |
| 2008/0161408 A1 * | 7/2008 | Frenkel et al. | 514/647 |
| 2009/0062400 A1 | 3/2009 | Oron et al. | |
| 2009/0076160 A1 | 3/2009 | Lendvai et al. | |
| 2009/0111892 A1 | 4/2009 | Patashnik et al. | |
| 2009/0181086 A1 | 7/2009 | Safadi et al. | |
| 2009/0312436 A1 | 12/2009 | Levy et al. | |
| 2010/0008983 A1 | 1/2010 | Safadi et al. | |
| 2010/0137447 A1 | 6/2010 | Lehmann et al. | |
| 2010/0144887 A1 | 6/2010 | Frenkel et al. | |
| 2010/0145101 A1 | 6/2010 | Frenkel et al. | |
| 2010/0168239 A1 | 7/2010 | Poewe | |
| 2010/0189788 A1 | 7/2010 | Safadi et al. | |
| 2010/0189790 A1 | 7/2010 | Safadi et al. | |
| 2010/0189791 A1 | 7/2010 | Safadi et al. | |
| 2011/0130466 A1 | 6/2011 | Lorenzl | |
| 2011/0152381 A1 | 6/2011 | Frenkel et al. | |
| 2012/0003310 A1 | 1/2012 | Safadi et al. | |

FOREIGN PATENT DOCUMENTS

| | | |
|---|---|---|
| WO | WO 2007/101400 | 9/2007 |
| WO | WO 2011/003938 | 1/2011 |

OTHER PUBLICATIONS

U.S. Appl. No. 12/456,643, filed Jun. 19, 2009, Anton Frenkel.
U.S. Appl. No. 12/456,029, filed Jun. 9, 2009, Safadi et al.
U.S. Appl. No. 12/456,031, filed Jun. 9, 2009, Safadi et al.
U.S. Appl. No. 12/455,976, filed Jun. 9, 2009, Safadi et al.
U.S. Appl. No. 12/456,001, filed Jun. 9, 2009, Safadi et al.
Jul. 8, 2009 Office Action issued in U.S. Appl. No. 12/002,082.
May 2, 2008 International Search Report for PCT International Application No. PCT/US07/025583.
Jun. 16, 2009 International Preliminary Report on Patentability and the Written Opinion of the International Searching Authority for Internat'l Appln. No. PCT/US07/025583.
U.S. Appl. No. 12/283,022, filed Sep. 8, 2009, Sterling et al.
U.S. Appl. No. 12/283,107, filed Sep. 8, 2008, Sterling et al.
U.S. Appl. No. 12/283,105, filed Sep. 8, 2008, Sterling et al.
U.S. Appl. No. 12/455,969, filed Jun. 10, 2009, Frenkel et al.
U.S. Appl. No. 13/281,054, filed Oct. 25, 2011 (Bahar et al.).
International Preliminary Report on Patentability and the Written Opinion of the International Searching Authority for International Application No. PCT/US2009/03677, issu.
International Preliminary Report on Patentability and the Written Opinion of the International Searching Authority for International Application No. PCT/US2009/03670, issu.
International Search Report for International Application No. PCT/US2009/03670, issued Oct. 5, 2009.

* cited by examiner

Figure 2. Effect of pressure and temperature on solid Rasagiline base sublimation rate

US 8,334,409 B2

PROCESS FOR PURIFYING RASAGILINE BASE

The application claims benefit of U.S. Provisional Application Nos. 61/132,512, filed Jun. 19, 2008, the contents of which are hereby incorporated by reference.

Throughout this application various publications and published patents are referenced. The disclosures of these publications in their entireties are hereby incorporated by reference into this application in order to more fully describe the state of the art to which this invention pertains.

BACKGROUND OF THE INVENTION

R(+)-N-propargyl-1-aminoindan ("R-PAI"), also known as rasagiline, has been reported to be a selective inhibitor of the B-form of the enzyme monoamine oxidase ("MAO-B") and is useful in treating Parkinson's disease and various other conditions.

Rasagiline mesylate is approved for treating Parkinson's disease either as monotherapy or as an adjunct with other treatments. See, e.g. AGILECT®, Physician's Desk Reference (2007), 61$^{st}$ Edition, Thomson Healthcare.

A synthesis of rasagiline is disclosed in U.S. Pat. No. 5,532,415 in which example 3 describes recovery of rasagiline base as an oil after chromatographic separation. The other synthetic examples in U.S. Pat. No. 5,532,415 show rasagiline salt preparation from its crude form or its racemic form which is further reacted with appropriate acids to form pharmaceutically acceptable salts.

The need for purification of rasagiline base and its corresponding racemic base is not disclosed, nor are appropriate methods for such purification.

SUMMARY OF THE INVENTION

The subject invention provides crystalline R(+)-N-propargyl-1-aminoindan and racemic N-propargyl-1-aminoindan characterized by colorless crystals.

The subject invention also provides a pharmaceutical composition comprising crystalline R(+)-N-propargyl-1-aminoindan characterized by colorless crystals and a pharmaceutically acceptable carrier.

The subject invention also provides a process for purification of N-propargyl-1-aminoindan comprising: a) introducing an amount of solid N-propargyl-1-aminoindan into a sublimation reservoir of a sublimation apparatus; b) cooling the sublimation reservoir and building up a vacuum in the sublimation reservoir; c) heating the sublimation reservoir so as to sublime the solid N-propargyl-1-aminoindan and to recrystallize the N-propargyl-1-aminoindan from the sublimed form; and d) recovering the recrystallized N-propargyl-1-aminoindan, thereby purifying the N-propargyl-1-aminoindan.

The subject invention also provides a process for preparing a pharmaceutical composition comprising crystalline N-propargyl-1-aminoindan and a pharmaceutically acceptable carrier, comprising: a) introducing an amount of solid N-propargyl-1-aminoindan into a sublimation reservoir of a sublimation apparatus; b) cooling the sublimation reservoir and building up a vacuum in the sublimation reservoir; c) heating the sublimation reservoir so as to sublime the solid N-propargyl-1-aminoindan and to recrystallize the N-propargyl-1-aminoindan from the sublimed form; d) recovering the recrystallized N-propargyl-1-aminoindan; and e) combining the recrystallized N-propargyl-1-aminoindan recovered in step d) with the pharmaceutically acceptable carrier, thereby preparing the pharmaceutical composition.

The subject invention also provides a process for producing a validated batch of a drug product containing crystalline N-propargyl-1-aminoindan and at least one pharmaceutically acceptable carrier for distribution comprising: a) producing a batch of the drug product; b) determining whether the crystalline N-propargyl-1-aminoindan in the batch is colorless; and c) validating the batch for distribution only if the crystalline N-propargyl-1-aminoindan in the batch is colorless.

The subject invention also provides an isolated liquid R(+)-N-propargyl-1-aminoindan containing greater than 98% R(+)-N-propargyl-1-aminoindan.

The subject invention also provides a pharmaceutical composition comprising liquid R(+)-N-propargyl-1-aminoindan characterized by a purity of R(+)-N-propargyl-1-aminoindan of greater than 98% by HPLC.

The subject invention also provides a process for producing the isolated liquid N-propargyl-1-aminoindan comprising:

a) introducing an amount of N-propargyl-1-aminoindan base into a sublimation reservoir of a sublimation apparatus;
b) cooling the sublimation reservoir and building up a vacuum in the sublimation reservoir;
c) heating the sublimation reservoir so as to sublime the N-propargyl-1-aminoindan and to recrystallize the N-propargyl-1-aminoindan from the sublimed form;
d) collecting the recrystallized N-propargyl-1-aminoindan from the sublimation head and heat the collected sublimed Rasagiline base into liquid; and
e) mixing the liquid Rasagiline base with a solvent.

The subject invention also provides a process for producing the isolated liquid N-propargyl-1-aminoindan comprising:

a) introducing an amount of crude N-propargyl-1-aminoindan into a distillation apparatus;
b) building up a vacuum in the distillation apparatus;
c) heating the distillation apparatus so as to evaporate the N-propargyl-1-aminoindan; and
d) collecting the distilled liquid N-propargyl-1-aminoindan; and
e) mixing the collected liquid N-propargyl-1-aminoindan with a solvent.

DETAILED DESCRIPTION OF THE INVENTION

Figure 1:
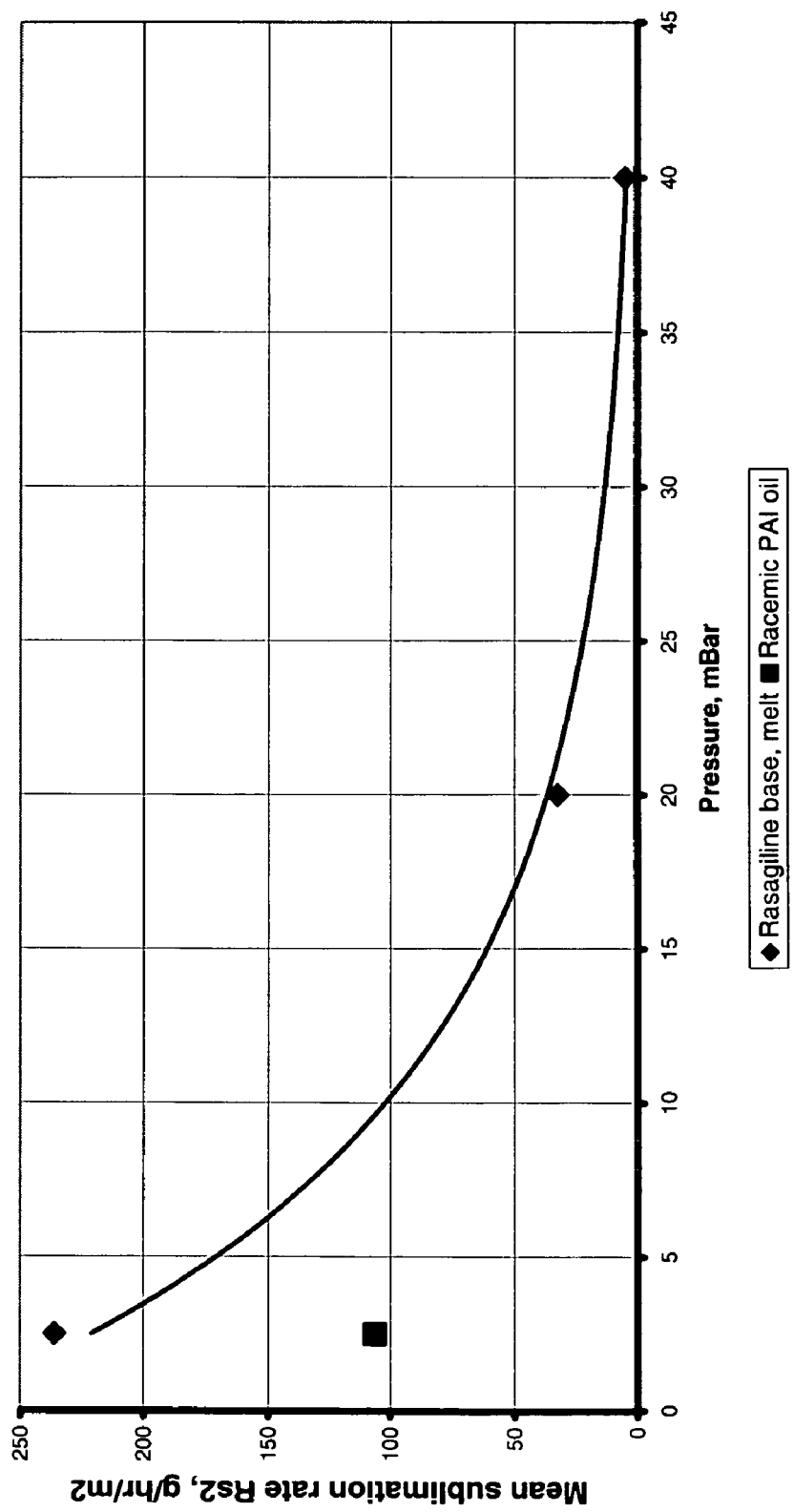
FIG. 1 shows the effect of pressure on evaporation/sublimation rate of liquid rasagiline base at 60° C.

The use and benefits of sublimation for rasagiline and racemic PAI base purification has not been disclosed in prior art.

The subject application provides crystalline R(+)-N-propargyl-1-aminoindan and racemic N-propargyl-1-aminoindan characterized by colorless crystals.

The subject application also provides a pharmaceutical composition comprising crystalline R(+)-N-propargyl-1-aminoindan characterized by colorless crystals and a pharmaceutically acceptable carrier.

By colorless, it is meant that the crystalline R(+)-N-propargyl-1-aminoindan is more white after the purification process by sublimation described herein.

In one embodiment, the pharmaceutical composition is formulated for oral administration. In another embodiment, the pharmaceutical composition is formulated for transdermal application. In yet another embodiment, the pharmaceutical composition is in the form of a transdermal patch.

The subject invention also provides a process for purification of N-propargyl-1-aminoindan comprising: a) introducing an amount of solid N-propargyl-1-aminoindan into a sublimation reservoir of a sublimation apparatus; b) cooling the sublimation reservoir and building up a vacuum in the sublimation reservoir; c) heating the sublimation reservoir so as to sublime the solid N-propargyl-1-aminoindan and to recrystallize the N-propargyl-1-aminoindan from the sublimed form; and d) recovering the recrystallized N-propargyl-1-aminoindan, thereby purifying the N-propargyl-1-aminoindan.

In one embodiment, the sublimation reservoir is heated to between 35° C.-200° C. In another embodiment, the sublimation reservoir is heated to between 45° C.-100° C. In yet another embodiment, the sublimation reservoir is heated to between 55° C.-75° C. In a yet another embodiment, the sublimation reservoir is heated to between 60° C.-70° C. In a yet another embodiment, the sublimation reservoir is heated to between 60° C.-100° C. In a yet another embodiment, the sublimation reservoir is heated to 60°.

In one embodiment, the pressure at the sublimation reservoir is 20 mbar or lower. In another embodiment, pressure at the sublimation reservoir is 10 mbar or lower.

In yet another embodiment, the pressure at the sublimation reservoir is 5 mbar or lower. In yet another embodiment, the pressure at the sublimation reservoir is 3 mbar or lower. In yet another embodiment, the pressure at the sublimation reservoir is 2 mbar or lower.

In embodiment, the sublimation reservoir is heated to between 35° C.-200° C. and the pressure at the sublimation reservoir is 20 mbar or lower. In another embodiment, the sublimation reservoir is heated to between 45° C.-100° C. and the pressure at the sublimation reservoir is 10 mbar or lower. In yet another embodiment, the sublimation reservoir is heated to between 55° C.-75° C. and the pressure at the sublimation reservoir is 5 mbar or lower. In yet another embodiment, the sublimation reservoir is heated to between 60° C.-70° C. and the pressure at the sublimation reservoir is 3 mbar or lower. In yet another embodiment, the sublimation reservoir is heated to between 60° C.-100° C. and the pressure at the sublimation reservoir is 3 mbar or lower. In yet another embodiment, the sublimation reservoir is heated to between 60° C.-70° C. and the pressure at the sublimation reservoir is 2 mbar or lower. In yet another embodiment, the sublimation reservoir is heated to between 60° C.-100° C. and the pressure at the sublimation reservoir is 2 mbar or lower.

The subject invention also provides a process for preparing a pharmaceutical composition comprising crystalline N-propargyl-1-aminoindan and a pharmaceutically acceptable carrier, comprising: a) introducing an amount of solid N-propargyl-1-aminoindan into a sublimation reservoir of a sublimation apparatus; b) cooling the sublimation reservoir and building up a vacuum in the sublimation reservoir; c) heating the sublimation reservoir so as to sublime the solid N-propargyl-1-aminoindan and to recrystallize the N-propargyl-1-aminoindan from the sublimed form; d) recovering the recrystallized N-propargyl-1-aminoindan; and e) combining the recrystallized N-propargyl-1-aminoindan recovered in step d) with the pharmaceutically acceptable carrier, thereby preparing the pharmaceutical composition.

The subject invention also provides a process for producing a validated batch of a drug product containing crystalline N-propargyl-1-aminoindan and at least one pharmaceutically acceptable carrier for distribution comprising: a) producing a batch of the drug product; b) determining whether the crystalline N-propargyl-1-aminoindan in the batch is colorless; and c) validating the batch for distribution only if the crystalline N-propargyl-1-aminoindan in the batch is colorless.

The subject invention also provides an isolated liquid R(+)-N-propargyl-1-aminoindan containing greater than 98% R(+)-N-propargyl-1-aminoindan.

In one embodiment, the isolated liquid R(+)-N-propargyl-1-aminoindan containing greater than 99.8% R(+)-N-propargyl-1-aminoindan.

In one embodiment, the isolated liquid R(+)-N-propargyl-1-aminoindan containing 100% R(+)-N-propargyl-1-aminoindan.

The subject invention also provides a pharmaceutical composition comprising liquid R(+)-N-propargyl-1-aminoindan characterized by a purity of R(+)-N-propargyl-1-aminoindan of greater than 98% by HPLC.

In one embodiment, the pharmaceutical composition The isolated liquid R(+)-N-propargyl-1-aminoindan characterized by a purity of R(+)-N-propargyl-1-aminoindan of greater than 99.8% R(+)-N-propargyl-1-aminoindan.

In another embodiment, the pharmaceutical composition The isolated liquid R(+)-N-propargyl-1-aminoindan characterized by a purity of R(+)-N-propargyl-1-aminoindan of 100% R(+)-N-propargyl-1-aminoindan.

In one embodiment, the pharmaceutical composition is formulated for oral administration.

In another embodiment, the pharmaceutical composition is formulated for transdermal application.

In yet another embodiment, the pharmaceutical composition is in the form of a transdermal patch.

The subject invention also provides a process for producing the isolated liquid N-propargyl-1-aminoindan comprising:

a) introducing an amount of N-propargyl-1-aminoindan base into a sublimation reservoir of a sublimation apparatus;

b) cooling the sublimation reservoir and building up a vacuum in the sublimation reservoir;

c) heating the sublimation reservoir so as to sublime the N-propargyl-1-aminoindan and to recrystallize the N-propargyl-1-aminoindan from the sublimed form;

d) collecting the recrystallized N-propargyl-1-aminoindan from the sublimation head and heat the collected sublimed Rasagiline base into liquid; and e) mixing the liquid Rasagiline base with a solvent.

In one embodiment of the process, in step a) the sublimation reservoir is heated to between 35° C. to 200° C.

In another embodiment of the process, the sublimation reservoir is heated to 60° C.

In yet another embodiment of the process, the in step b) the pressure at the sublimation reservoir is 20 mbar or lower.

In yet another embodiment of the process, the pressure at the sublimation reservoir is 3 mbar or lower.

In yet another embodiment of the process, the in step e) the solvent is a pharmaceutically acceptable solvent.

In yet another embodiment of the process, the solvent is ethanol.

The subject invention also provides a process for producing the isolated liquid N-propargyl-1-aminoindan comprising:

a) introducing an amount of crude N-propargyl-1-aminoindan into a distillation apparatus;
b) building up a vacuum in the distillation apparatus;
c) heating the distillation apparatus so as to evaporate the N-propargyl-1-aminoindan;
d) collecting the distilled liquid N-propargyl-1-aminoindan; and
e) mixing the collected liquid N-propargyl-1-aminoindan with a solvent.

In an embodiment of the process, in step a) the distillation apparatus is heated to between 35° C. to 55° C.

In another embodiment of the process, the distillation apparatus is heated to 40° C.

In yet another embodiment of the process, the in step b) the pressure in the distillation apparatus is 20 mbar or lower.

In yet another embodiment of the process, the pressure in the distillation apparatus is 3 mbar or lower.

In yet another embodiment of the process, in step e) the solvent is a pharmaceutically acceptable solvent.

In yet another embodiment of the process, the pharmaceutically acceptable solvent is ethanol, PEG 400, vegetable oil, or glycerol.

In yet another embodiment of the process, the pharmaceutically acceptable solvent is PEG 400.

By a temperature of between 35° C.-200° C., it is meant that all tenth and integer degrees Celsius within the range are specifically disclosed as part of the invention. Thus, 35.1, 35.2, 35.2° C. . . . 199.8, 199.9, and 36, 37, 38° C., . . . 197, 198, 199° C. are disclosed as embodiments of this invention. Similarly, by a pressure of 20 mbar or lower, it is meant that all tenth and integer percentages within the range are specifically disclosed as part of the invention. Thus, 19.9, 19.8, 19.7 mbar, . . . and 19, 18, 17 mbar, . . . and so on are included as embodiments of this invention.

As used herein, "PAI" refers to N-propargyl-1-aminoindan.

As used herein, "drug substance" refers to the active ingredient in a drug product, which provides pharmacological activity or other direct effect in the diagnosis, cure, mitigation, treatment, or prevention of disease, or to affect the structure of any function of the body of man or animals.

As used herein, "drug product" refers to a pharmaceutical composition in finished dosage form containing the drug substance as well as at least one pharmaceutically acceptable carrier.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life.

R(+)-N-propargyl-1-aminoindan can be obtained in the crystalline form characterized by a powder X-ray diffraction pattern having peaks at 8.5, 12.6, 16.1, and 16.9 in degrees two theta±0.2. It can be further characterized by an X-ray powder diffraction pattern having peaks at 20.3, 20.9, 25.4, 26.4, and 28.3 in degrees two theta±0.2; or by a melting point of 38-41° C.

A process for the manufacture of crystalline R(+)-N-propargyl-1-aminoindan comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

Another process for the manufacture of crystalline R(+)-N-propargyl-1-aminoindan comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a second residue; and e) maintaining the second residue at a temperature between 0 and 25° C. to form crystalline R(+)-N-propargyl-1-aminoindan.

Yet another process for the manufacture of crystalline R(+)-N-propargyl-1-aminoindan comprises a) obtaining a solution of R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan.

Crystalline rasagiline base has lower water solubility than many rasagiline salts, especially the mesylate salt, which is water soluble. The solubility of rasagiline mesylate in water is 92 mg/ml at a pH of 6.7 and 570 mg/ml at a pH of 3.3, both measured at 25° C. At the same temperature, the solubility of rasagiline base in water is 5.5 mg/ml at a pH of 11.

Crystalline rasagiline base may be used as a synthetic intermediate to be used to attain a rasagiline salt, such as rasagiline mesylate or rasagiline tartrate. The crystalline rasagiline base may be dissolved in a solvent and reacted with an acid to form a pharmaceutically acceptable acid addition salt. The crystallization of rasagiline base could provide additional purification of the acid addition salt.

Water solubility is often an important characteristic of an active pharmaceutical ingredient, especially when formulating oral compositions. Sometimes, lipophilicity of an active pharmaceutical ingredient is desired when formulating other pharmaceutical compositions. Crystalline rasagiline base may be useful for formulating pharmaceutical compositions wherein low solubility in water is desired. For example, compositions for transdermal administrations can be formulated from lipophilic compounds. Examples of such transdermal compositions include ointments, creams and patches.

Specific examples of pharmaceutical acceptable carriers and excipients that may be used to formulate oral dosage forms are described, e.g., in U.S. Pat. No. 6,126,968 to Peskin et al., issued Oct. 3, 2000. Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S.

Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

U.S. Pat. No. 6,126,968, the entire contents of which are incorporated herein by reference, disclosed that the stability of formulations comprising PAI can be significantly improved by the incorporation of relatively large amounts of certain alcohols. In particular, the alcohol is selected from the group of pentahydric or hexahydric alcohols (U.S. Pat. No. 6,126,968). The alcohol is typically selected from mannitol, xylitol or sorbitol (U.S. Pat. No. 6,126,968). The composition may further comprise citric acid (U.S. Pat. No. 6,126,968).

(R)-PAI itself may be prepared, for example, according to the process described in Example 6B of WO 95/11016.

Transdermal Formulations and Transdermal Patches

Transdermal Formulations are medicated adhesive patches placed on the skin to deliver a time-released dose of medication through the skin and into the bloodstream. A wide variety of pharmaceuticals can be delivered through transdermal patches, such as nicotine for smoking cessation, scopolamine for motion sickness, estrogen for menopause, and prevention of osteoporosis, nitroglycerin for angina, lidocaine for pain relief from shingles. Some pharmaceuticals must be combined with other substances, such as alcohol, to increase their ability to penetrate the skin. Molecules of insulin, and many other pharmaceuticals, however, are too large to pass through the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. ("Transdermal Patches" Wikipedia, Nov. 15, 2007, Wikipedia Foundation, Inc., Dec. 13, 2007 http://en.wikipedia.org/wiki/Transdermal_patch; and Remington, The Science and Practice of Pharmacy, $20^{th}$ Edition, 2000)

In reservoir type patches, a drug is combined with a non-volatile, insert liquid, such as mineral oil, whereas drug in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST PRESENT, FUTURE," Molecular Interventions, 4:308-312) The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Deliver)

Rasagiline may also be used in combination with other drug in a transdermal patch, such as Levodopa, L-carbidopa, benserazide, ladostigil, or riluzole.

EXPERIMENTAL DETAILS

Set 1

Initial Preparation of Rasagiline Crystals

Example 1

Isolation of Rasagiline Base by Splitting and Extraction

Rasagiline mesylate was prepared essentially as described in U.S. Pat. No. 5,532,415 example 6B, with the exception that the tartrate salt was split by addition of NaOH, and the rasagiline free base was isolated as an oil. The mesylate salt was then formed by addition of methanesulfonic acid.

120 g of rasagiline mesylate were dissolved in 700 ml of deionized water. 400 ml of toluene were added and the mixture was basified with 25% NaOH solution to a pH of about 14. After stirring, two phases separated. The lower water phase was extracted with 200 ml of toluene. The phases were allowed to separate and the aqueous phase was discarded.

The two toluenic extractions were combined and the solvent was distilled under vacuum. The yield of rasagiline base was 88.5 g of a yellowish oil with a melting point of below 20° C.

25.1 g of the liquid rasagiline base was sampled. The sample was mixed with ethanol and the solvent was distilled under vacuum. 22.6 g of the rasagiline base residue, in the form of a yellowish oil remained after the ethanol evaporation. The rasagiline base in oil form remained in oil form for a number of weeks, and did not crystallize spontaneously.

Example 2

Isolation of Rasagiline Base by Splitting and Extraction 155 g of rasagiline tartrate, prepared essentially as described in U.S. Pat. No. 5,532,415 example 6B, and 20 g of rasagiline mesylate, prepared as described in example 1, were dissolved in 800 ml of water. 400 ml of toluene were added to the solution and the mixture was basified with 25% NaOH solution to a pH of about 14 and heated to 45±5° C.

After stirring, two phases were separated. The lower water phase was extracted twice with 300 ml of toluene at 45±5° C. The organic phases were combined and the aqueous phase was discarded.

The combined organic phase was washed with 200 ml of deionized water. Then the solvent was distilled under vacuum and 50 ml isopropanol were added to the resulting residue. The solvent was removed by vacuum and additional 50 ml isopropanol were added and then removed by vacuum. 100 g of syrup-like liquid rasagiline base were formed.

Example 3

Splitting and Spontaneous Crystallization from Water 15 g of rasagiline mesylate were dissolved in 150 ml water while stirring. The solution was cooled to 5° C. and 25% NaOH solution was added slowly. During the addition, batch temperature was maintained between 3 and 5° C. Solid precipitation was observed after reaching a pH of 7.5. After reaching a pH of 11, the NaOH addition was stopped, the batch was stirred while cooling for one hour and filtered. The filtration proceeded quickly. The solid product was washed with water on the filter and dried under vacuum.

8.8 g of solid dried rasagiline base were attained. The yield was 91.6%. The melting point of the solid was determined to be 38.2-38.4° C.

Example 4

Melt Crystallization 6 g of rasagiline base liquid in syrup-like form, from example 1, after toluenic evaporation were dissolved in 20 ml of isopropanol. The solution was evaporated in a warm water bath using a rotating evaporator under 12 mbar vacuum until complete solvent removal. The residue was then dissolved in an additional 20 ml of isopropanol and the evaporation was repeated. The resulting residue crystallized spontaneously at room temperature after a few hours. The solid crystalline residue was determined to be rasagiline base. 5.2 g of the solid crystalline base were attained. The yield was quantitative.

Example 5

Addition of Rasagiline Ethanolic Solution to Water 2.4 g of rasagiline base from example 1 were dissolved in 2.4 g of ethanol. The solution was added dropwise to 5 ml of cold (0-5° C.) water while stirring, and a white precipitate was formed during the addition. The resulting mixture was stirred while cooling for about 30 minutes and was filtered. The filtration proceeded quickly, and the solid product was dried to constant mass under vacuum.

2.15 g of solid crystalline rasagiline were attained, with a yield of 89.6%.

Analysis: Chromatographic purity by HPLC ~100%, Assay by HPLC-99.0%.

Example 6

Addition of Water to Rasagiline Ethanolic Solution 3 g of rasagiline base from example 1 were dissolved in 5 ml of ethanol. The solution was stirred at room temperature and 4.5 ml of water were added. No precipitation occurred. The resulting solution was cooled, and at 12° C. precipitation of a white material was observed. The mixture was cooled to ~0° C., stirred at this temperature for 30 min, and filtered. The filtration proceeded quickly. The solid product was washed with water on the filter and was dried under vacuum.

2.72 g of solid crystalline rasagiline were attained, with a yield of 90.0%.

Analysis: Chromatographic purity by HPLC ~100%, Assay by HPLC-100.0%.

Example 7

Addition of Rasagiline Isopropanolic Solution to Water 8.2 g of rasagiline base from example 1 were dissolved in 10 ml of isopropanol and the solution was stirred at room temperature. 14 ml of water were added. No precipitation occurred. The resulting solution was cooled, and at 17° C. precipitation of white material was observed. 20 ml of deionized water were added to the mixture and the mixture was further cooled to ~0° C., stirred at this temperature for 30 min, and filtered.

The filtration proceeded quickly. The solid product was washed with water on the filter and dried under vacuum. 5.96 g of solid crystalline rasagiline were attained, with a yield of 72.7%.

Analysis: Chromatographic purity by HPLC ~100%, Assay by HPLC-99.7%

Example 8

Addition of Water to Rasagiline Isopropanolic Solution

Crop A 148 g of rasagiline base (48.0 g from example 1, and 100.0 g from example 2) were dissolved in 180 ml of isopropanol. The solution was cooled to 17° C. and 252 ml of deionized water were added at this temperature. The solution was cooled to 10° C. and seeded with solid rasagiline base. Immediate crystallization was observed. 100 ml of water were then added to the mixture. The mixture was cooled to 1° C., stirred at this temperature for 30 min and filtered. The solid was washed on the filter with 200 ml of water and dried under vacuum.

138.9 g of solid, crystalline rasagiline were attained, with a yield of 93.8%. The melting point in an open capillary was determined to be 39.0-39.2° C.

Analysis: Chromatographic purity by HPLC ~100%, Assay by HPLC-98.5%.

Crop B

The mother liquor and washing liquor from crop A were combined, and solid product precipitated from the mixture. Yellowish material was separated by filtration and dried under vacuum.

1.5 g of solid, crystalline rasagiline base were attained, with a yield of 1.0%.

DISCUSSION

The solid crystalline rasagiline base which was synthesized in examples 3-8 was found to be of high purity.

The same melting point value (41° C. by differential scanning calorimetry (DSC) or 38-39° C. in an open capillary) was measured for all batches of the crystalline rasagiline base. Low levels of volatiles (water and residual solvents) were found by Karl Fischer (KF) and by thermogravimetric analysis (TGA) methods. This indicated that crystalline rasagiline base is not hygroscopic.

Crystalline rasagiline base was found freely soluble in polar and non-polar organic solvents—alcohols, acetone, ethyl acetate, toluene, diethyl ether, dioxane, hexane and n-heptane.

All batches of solid rasagiline base were found highly crystalline by powder X-ray diffraction (XRD) and DSC method. Characteristic XRD and Fourier Transfer Infrared (FTIR) patterns and reproducible narrow melting range and enthalpy show the same polymorphic composition of all experimental batches from examples 3-8. The crystal form was designated as Form I.

The X-Ray Diffraction equipment used was a Scintag X-Ray powder diffractometer model X'TRA, Cu-tube, solid state detector.

Sample holder: a round standard aluminum sample holder with round zero background quartz plate with cavity of 25 (diameter)*0.5 (dept.) mm.

Scanning parameters: Range: 2-40 degrees two-theta.

Scan mode: Continuous scan

Step size: 0.05 deg.

Rate: 5 deg./min.

The peaks of a sample prepared according to Example 4 are listed below. The most characteristic peaks are listed in bold.

| Form I |
|---|
| 8.5 |
| 12.6 |
| 16.1 |
| 16.9 |
| 20.3 |
| 20.9 |
| 25.4 |
| 26.4 |
| 28.3 |

FTIR analysis of the samples was performed as follows:

Equipment: Perkin Elmer Spectrum One FT-IR Spectrometer S/N 58001.

Parameters: The samples were studied in DRIFT mode. All the spectra were measured in 16 scans. Resolution: 4.0 cm$^{-1}$.

All samples of solid rasagiline base prepared in this study appear as white crystalline powder (with the exception of Crop B from example which was isolated as a yellowish powder.) Microscopic observation shows that the crystallization conditions strongly affect the particle size and morphology. Seeded crystallization provides large regular non-aggregated crystals while spontaneous precipitation resulted in formation of small aggregated particles. The difference in the particle morphology is not related to polymorphism.

The morphology and particle size of the crystalline rasagiline base from the examples above is shown in the table below. The morphology and particle size was determined by microscopic observation.

| Example No. | Morphology | Particle Size Range (µm) |
|---|---|---|
| 4 | Irregular particles | 250-1000 |
| 5 | Small rods | 5-50 |
| 6 | Rods | 30-150 |
| 7 | Small aggregated rods | 5-50 |
| 8 | Rods | 250-2000 |

Starting Materials for Examples 9, 10 and 11:

(1) Wet Rasagiline Hemi Tartrate containing ~10-15% residual solvent and 0.7% S-isomer.

(2) Racemic RAI base, oil, PAI content-94% by HPLC.

Example 9

Splitting and Precipitation from Isopropanol-Water, Seeded Emulsion Crystallization 70.0 g of Rasagiline Tartrate salt (1) suspended in 320 ml deionized water at stirring. The suspension heated to 45° C. and 31 ml of 25% NaOH solution was added with 160 ml Toluene. The mixture was stirred and the resulting emulsion was settled. Two phases were separated. The lower aqueous phase (pH=13-14) was discarded. The upper toluenic phase was washed with 100 ml deionized water at 45° C. and settled. Lower aqueous phase (pH=9-10) was discarded.

Toluenic solution was evaporated under vacuum in evaporator, after the solvent evaporation completion 50 ml isopropanol was added to the residue and evaporation was continued.

After completion of the evaporation 25 ml of isopropanol was added and distilled out under the same conditions.

The residue, oil of R-PAI base (33.9 g), was dissolved in 41 ml isopropanol.

The solution was cooled to 15° C. and 58 ml of deionized water was added by portions in 2 hr at cooling and stirring. During the addition of water oily precipitate was formed. The resulting emulsion of oil in water was stirred at 1-3° C. for one hour, no crystallization was observed.

The batch was seeded with crystalline Rasagiline base at 1-3° C. and immediate exothermic crystallization took place. 50 ml of water was added to the resulting slurry to improve stirrability and flowability. The batch was stirred for additional 30 minutes and filtered. The solid was washed with water and dried at room temperature under vacuum.

31.5 g of solid dry R-PAI base were attained, with a yield of 92% on oil base. FIG. 11 is a micrograph of this rasagiline base.

Analysis: Melting point (by DSC)-40.8° C., S-isomer by HPLC 0.02%, Purity by HPLC-100%, Assay by HPLC-98%.

Example 10

Splitting and Precipitation from Isopropanol-Water, Seeded Crystallization from Solution Isopropanol-Water 100.0 g of Rasagiline Tartrate (1) was suspended in 458 ml deionized water, 229 ml Toluene was added and 46 ml of 25% NaOH solution was introduced at stirring. The mixture was heated to 45° C., stirred at 45 C for 15 minutes and settled at this temperature.

Two phases were separated. The lower aqueous phase (pH=13-14) was discarded, the upper toluenic phase was washed with 140 ml deionized water. The resulting emulsion was settled, and two phases were separated. The lower aqueous phase (pH=9-10) was discarded, the toluenic solution was evaporated under vacuum in evaporator.

After the solvent evaporation completion 60 ml isopropanol was added to the residue and evaporation was continued.

After completion of the evaporation 50 ml of isopropanol was added and distilled out under the same conditions.

The residue, oil of R-PAI base (46.4 g), was dissolved in 56 ml isopropanol.

The solution was cooled to 16° C. and 147.5 ml of deionized water was added by portions in 3 hr at cooling and stirring. During the addition of water precipitation development was observed and the batch was immediately seeded with crystalline R-PAI base.

The resulting suspension was cooled to 2° C., stirred at this temperature overnight and filtered. The solid was washed with water and dried at room temperature under vacuum.

48.1 g of Solid dry R-PAI base were attained, with a yield of 96% on oil base. FIG. 12 is a micrograph of this rasagiline base.

Analysis: Melting point (by DSC)-41.3° C., S-isomer by HPLC 0.01%, Purity by HPLC-100%, Assay by HPLC-96%

Example 11

Racemic PAI Base Crystallization (AF-8026) Precipitation from Isopropanol-Water 51.0 g of racemic PAI base oil (2) dissolved in 50 ml isopropanol. The solvent was distilled out of the solution under vacuum at evaporator.

The residue (49.4 g) was dissolved in 60 ml isopropanol, stirred and cooled. 156 ml of deionized water was added by portions in 3 hr at cooling and stirring. During the addition of water oily precipitate was formed. The batch was seeded with crystalline Rasagiline base, no crystallization was observed.

The resulting emulsion of oil in water was stirred at 3° C. for 1 hour, no crystallization was observed.

The batch was crystallized spontaneously during stirring overnight at 1° C. The solid was filtered, but during the filtration it began to melt. At room temperature the solid product completely liquefied on the filter in 1-2 min.

The material was sampled before the melting completion.

Analysis: S-isomer by HPLC 49.4%, Assay by HPLC-87%.

DISCUSSION

Examples 9, 10 and 11 presented above show that the ability to crystallize at room temperature is an intrinsic property of pure Rasagiline base (R-isomer). Racemic PAI base exists at room temperature only in liquid form, its melting point being between 1 and 18° C. (Example 11).

The Examples also show that crystallization of Rasagiline base contaminated with S-isomer provides significant purification of the crystallized product. Starting material containing 0.7% of S-isomer was processed into solid crystalline Rasagiline base with only 0.01-0.02% of S-isomer.

Examples 9, 10 and 11 also show the same trend in Particle Size of the crystallized product as was described in previous Examples. The slow seeded crystallization at 10-16° C. (Example 9) provides higher particle size of Rasagiline base than emulsion crystallization at 1-3° C. (Example 10).

CONCLUSIONS

The above experiments demonstrate varying processes for manufacturing crystalline R(+)-N-propargyl-1-aminoindan.

The first process for manufacture of crystalline R(+)-N-propargyl-1-aminoindan comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

Another process for manufacture of crystalline R(+)-N-propargyl-1-aminoindan comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a residue; and e) maintaining the second residue at a temperature between 0 and 25° C. to form crystalline R(+)-N-propargyl-1-aminoindan.

Yet another process for manufacture of crystalline R(+)-N-propargyl-1-aminoindan comprises: a) obtaining a solution of crystalline R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan. The resulting crystalline R(+)-N-propargyl-1-aminoindan can be characterized by a powder X-ray diffraction pattern having peaks at 8.5, 12.6, 16.1, and 16.9 in degrees two theta±0.2.

The crystalline rasagiline base can further be characterized by an X-ray powder diffraction pattern having peaks at 20.3, 20.9, 25.4, 26.4, and 28.3 in degrees two theta±0.2.

The crystalline rasagiline base can further be characterized by a melting point of 38-39° C. when determined in an open capillary or 41° C. when determined by differential scanning calorimetry.

However, the crystalline rasagiline base obtained using the foregoing examples were not colorless. Accordingly, further purification processing was undertaken.

Set 2

N-propargyl-1-aminoindan Purification by Sublimation

Example 12

Sublimation Of Rasagiline Base at 2-3 mbar Pressure and 21° C. Temperature

Approximately four (4) grams of rasagiline base was introduced into the sublimation reservoir of a standard Sigma-Aldrich glass sublimation apparatus, (Cat. No. Z221171-1EA) with internal diameter of 3 cm. The apparatus was equipped with vacuum pump, vacuumeter and circulating ice-water bath for cooling of the apparatus' sublimation head. The apparatus was then closed and circulation of coolant at 0 to 1° C. was started. The vacuum was then built to a pressure ("P") of 2-3 mbar and the reservoir was introduced into thermostatic water bath maintained at temperature ("T") of 21° C.

The process was controlled by visual observation of the sublimed solid forming on the sublimation head. After sublimation completed the operation time was recorded, the apparatus was opened and the sublimed solid was removed from the head and weighed.

The mean sublimation rate was calculated as follows:
Mean sublimation rate $R_{s1}$:

$$R_{s1} = m/M \cdot t \, [g \, g^{-1} \, hr^{-1}]$$

Mean sublimation rate $R_{s2}$:

$$R_{s2} = m/S \cdot t \, [g \, m^{-2} \, hr^{-1}]$$

Mean relative sublimation rate R:

$$R = m \cdot 100/M \cdot t \, [\%/hr]$$

m—mass of sublimed material, g
M=mass of starting material, g
t=sublimation time, hrs
S=sublimation area (apparatus section area), $m^2$ After 8 hours, 10 mg of sublimed rasagiline were attained, with a yield of 0.25%. The mean sublimation rates were $R_{s1}=3.12\times10^{-5}$ g g$^{-1}$ hr$^{-1}$; $R_{s2}=1.333$ g m$^{-2}$ hr$^{-1}$; and R=0.0312%/hr.

Example 13

Sublimation of Rasagiline Base at 2-3 mbar Pressure and 35° C. Temperature

The experimental steps from Example 1 was used with the exception that T=35° C.

After 5.33 hours, 25 mg of sublimed rasagiline were attained, with a yield of 0.62%. The mean sublimation rates were $R_{s1}=1.17\times10^{-3}$ g g$^{-1}$ hr$^{-1}$; $R_{s2}=4.978$ g m$^{-2}$ hr$^{-1}$; and R=0.116%/hr.

Example 14

Sublimation of Rasagiline Base at 2-3 mbar Pressure and 60° C. Temperature

The experimental steps from Example 1 was used with the exception that T=60° C. At 60° C., starting rasagiline was liquid (melt).

After 4.0 hours, 890 mg of sublimed rasagiline were attained, with a yield of 22.4%. The mean sublimation rates were $R_{s1}=5.62\times10^{-2}$ g g$^{-1}$ hr$^{-1}$; $R_{s2}=236.19$ g m$^{-2}$ hr$^{-1}$; and R 5.6%/hr.

Example 15

Sublimation of Rasagiline Base at 20 mbar Pressure and 21° C. Temperature

The experimental steps from Example 1 was used with the exception that P=20 mbar.

After 8.5 hours, 0 mg of sublimed rasagiline were attained, with a yield of 0.0%. The mean sublimation rates were $R_{s1}=0.0$ g g$^{-1}$ hr$^{-1}$; $R_{s2}=0.0$ g m$^{-2}$ hr$^{-1}$; and R=0.0%/hr.

Example 16

Sublimation of Rasagiline Base at 40 mbar Pressure and 21° C. Temperature

The experimental steps from Example 1 was used with the exception that P=40 mbar.

After 8.5 hours, 0 mg of sublimed rasagiline were attained, with a yield of 0.0%. The mean sublimation rates were $R_{s1}=0.0$ g g$^{-1}$ hr$^{-1}$; $R_{s2}=0.0$ g m$^{-2}$ hr$^{-1}$; and R=0.0%/hr.

Example 17

Sublimation of Rasagiline Base at 40 mbar Pressure and 35° C. Temperature

The experimental steps from Example 1 was used with the exception that T=35° C. and P=40 mbar.

After 5.33 hours, 8 mg of sublimed rasagiline were attained, with a yield of 0.20%. The mean sublimation rates were $R_{s1}=3.75\times10^{-4}$ g g$^{-1}$ hr$^{-1}$; $R_{s2}=1.593$ g m$^{-2}$ hr$^{-1}$; and R=0.0375%/hr.

Example 18

Sublimation of Rasagiline Base at 20 mbar Pressure and 35° C. Temperature

The experimental steps from Example 1 was used with the exception that T=35° C. and P=20 mbar.

After 5.33 hours, 11 mg of sublimed rasagiline were attained, with a yield of 0.27%. The mean sublimation rates were $R_{s1}=5.15\times10^{-4}$ g g$^{-1}$ hr$^{-1}$; $R_{s2}=2.192$ g m$^{-2}$ hr$^{-1}$; and R=0.0506%/hr.

Example 19

Sublimation of Rasagiline Base at 40 mbar Pressure and 60° C. Temperature

The experimental steps from Example 1 was used with the exception that T=60° C. and P=40 mbar. At 60° C., starting rasagiline was liquid (melt).

After 5.33 hours, 25 mg of sublimed rasagiline were attained, with a yield of 0.62%. The mean sublimation rates were $R_{s1}=1.17\times10^{-3}$ g g$^{-1}$ hr$^{-1}$; $R_{s2}=4.978$ g m$^{-2}$ hr$^{-1}$; and R=0.116%/hr.

Example 20

Sublimation of Rasagiline Base at 20 mbar Pressure and 60° C. Temperature

The experimental steps from Example 1 was used with the exception that T=60° C. and P=20 mbar. At 60° C., starting rasagiline was liquid (melt).

After 5.33 hours, 162 mg of sublimed rasagiline were attained, with a yield of 4.1%. The mean sublimation rates were $R_{s1}=7.64\times10^{-3}$ g g$^{-1}$ hr$^{-1}$; $R_{s2}=32.26$ g m$^{-2}$ hr$^{-1}$; and R=0.769%/hr.

Example 21

Sublimation of Racemic PAI Oil at 20 mbar Pressure and 22° C. Temperature

The experimental steps from Example 1 was used with the exception that the starting material is racemic PAI oil, T=22° C., and P=20 mbar.

After 8 hours, 0 mg of sublimed racemic PAI were attained, with a yield of 0.0%. The mean sublimation rates were $R_{s1}=0.0$ g g$^{-1}$ hr$^{-1}$; $R_{s2}=0.0$ g m$^{-2}$ hr$^{-1}$; and R=0.0%/hr.

Example 22

Sublimation of Racemic PAI Oil at 20 mbar Pressure and 35° C. Temperature

The experimental steps from Example 1 was used with the exception that the starting material is racemic PAI oil, T=35° C., and P=20 mbar.

After 5.33 hours, 0 mg of sublimed racemic PAI were attained, with a yield of 0.0%. The mean sublimation rates were $R_{s1}=0.0$ g g$^{-1}$ hr$^{-1}$; $R_{s2}=0.0$ g m$^{-2}$ hr$^{-1}$; and R=0.0%/hr.

Example 23

Sublimation of Racemic PAI Oil at 2-3 mbar Pressure and 22° C. Temperature

The experimental steps from Example 1 was used with the exception that the starting material is racemic PAI oil and T=22° C.

After 3.0 hours, 10 mg of sublimed racemic PAI were attained, with a yield of 0.25%. The mean sublimation rates were $R_{s1}=8.33\times10^{-4}$ g g$^{-1}$ hr$^{-1}$; $R_{s2}=3.537$ g m$^{-2}$ hr$^{-1}$; and R=0.08%/hr.

Example 24

Sublimation of Racemic PAI Oil at 2-3 mbar Pressure and 60° C. Temperature

The experimental steps from Example 1 was used with the exception that the starting material is racemic PAI oil and T=60° C.

After 1.3 hours, 130 mg of sublimed racemic PAI were attained, with a yield of 3.25%. The mean sublimation rates were $R_{s1}=2.50\times10^{-2}$ g g$^{-1}$ hr$^{-1}$; $R_{s2}=101.16$ g m$^{-2}$ hr$^{-1}$; and R=2.5%/hr.

SUMMARY OF RESULTS

The starting material (solid rasagiline base, melt rasagiline base, or racemic PAI), the sublimation conditions, the yield after sublimation, and the mean sublimation rates of the examples are listed in the Table 1 below.

TABLE 1

Effect of process parameters on PAI sublimation rates

| Example No. | Starting material Compound | Weight g | Sublimation conditions Pressure mbar | Temp. °C. | Time hr | Sublimed solid weight mg | fraction %* | Mean sublimation rate $R_{s1}$ g/g/hr | $R_{s2}$ g/hr/m$^2$ | R %/hr | $-\log R_{s1}$ |
|---|---|---|---|---|---|---|---|---|---|---|---|
| 12 | Solid R-PAI | 4.0 | 2-3 | 21 | 8.0 | 10 | 0.25 | 3.12 10$^{-5}$ | 1.333 | 0.0312 | 4.5 |
| 13 | Solid R-PAI | 3.99 | 2-3 | 35 | 5.33 | 25 | 0.62 | 1.17 10$^{-3}$ | 4.978 | 0.116 | 2.93 |
| 14 | Melt R-PAI | 3.965 | 2-3 | 60 | 4.0 | 890 | 22.4 | 5.62 10$^{-2}$ | 236.19 | 5.6 | 1.25 |
| 15 | Solid R-PAI | 4.0 | 20 | 21 | 8.5 | 0 | 0.0 | 0.0 | 0.0 | 0.0 | — |
| 16 | Solid R-PAI | 4.0 | 40 | 21 | 8.5 | 0 | 0.0 | 0.0 | 0.0 | 0.0 | — |
| 17 | Solid R-PAI | 4.0 | 40 | 35 | 5.33 | 8 | 0.20 | 3.75 10$^{-4}$ | 1.593 | 0.0375 | 3.42 |
| 18 | Solid R-PAI | 3.992 | 20 | 35 | 5.33 | 11 | 0.27 | 5.15 10$^{-4}$ | 2.192 | 0.0506 | 3.29 |
| 19 | Melt R-PAI | 4.0 | 40 | 60 | 5.33 | 25 | 0.62 | 1.17 10$^{-3}$ | 4.978 | 0.116 | 2.93 |
| 20 | Melt R-PAI | 3.975 | 20 | 60 | 5.33 | 162 | 4.1 | 7.64 10$^{-3}$ | 32.26 | 0.769 | 2.12 |
| 21 | Rac. PAI oil | 4.0 | 20 | 22 | 8.0 | 0 | 0.0 | 0.0 | 0.0 | 0.0 | — |
| 22 | Rac. PAI oil | 4.0 | 20 | 35 | 5.33 | 0 | 0.0 | 0.0 | 0.0 | 0.0 | — |
| 23 | Rac. PAI oil | 4.0 | 2-3 | 22 | 3.0 | 10 | 0.25 | 8.33 10$^{-4}$ | 3.537 | 0.08 | 3.08 |
| 24 | Rac. PAI oil | 4.0 | 2-3 | 60 | 1.3 | 130 | 3.25 | 2.50 10$^{-2}$ | 101.16 | 2.5 | 1.60 |

DISCUSSION

The data show that rasagiline base and racemic PAI base have similar sublimation ability, i.e., the sublimation rates of the R-isomer and racemic mixture are similar.

Sublimed racemic PAI base was obtained as colorless crystals at 0±1° C. but at room temperature it was liquefied into colorless oil. This observation is consistent with the finding that the melting point of this compound is about 8° C.

Sublimed rasagiline base was obtained as large (few millimeters size) colorless crystals with melting point 39-41° C. and has the same polymorph modification as the solid crystallized directly from solution in Experimental Details—Set 1.

Figure 2:
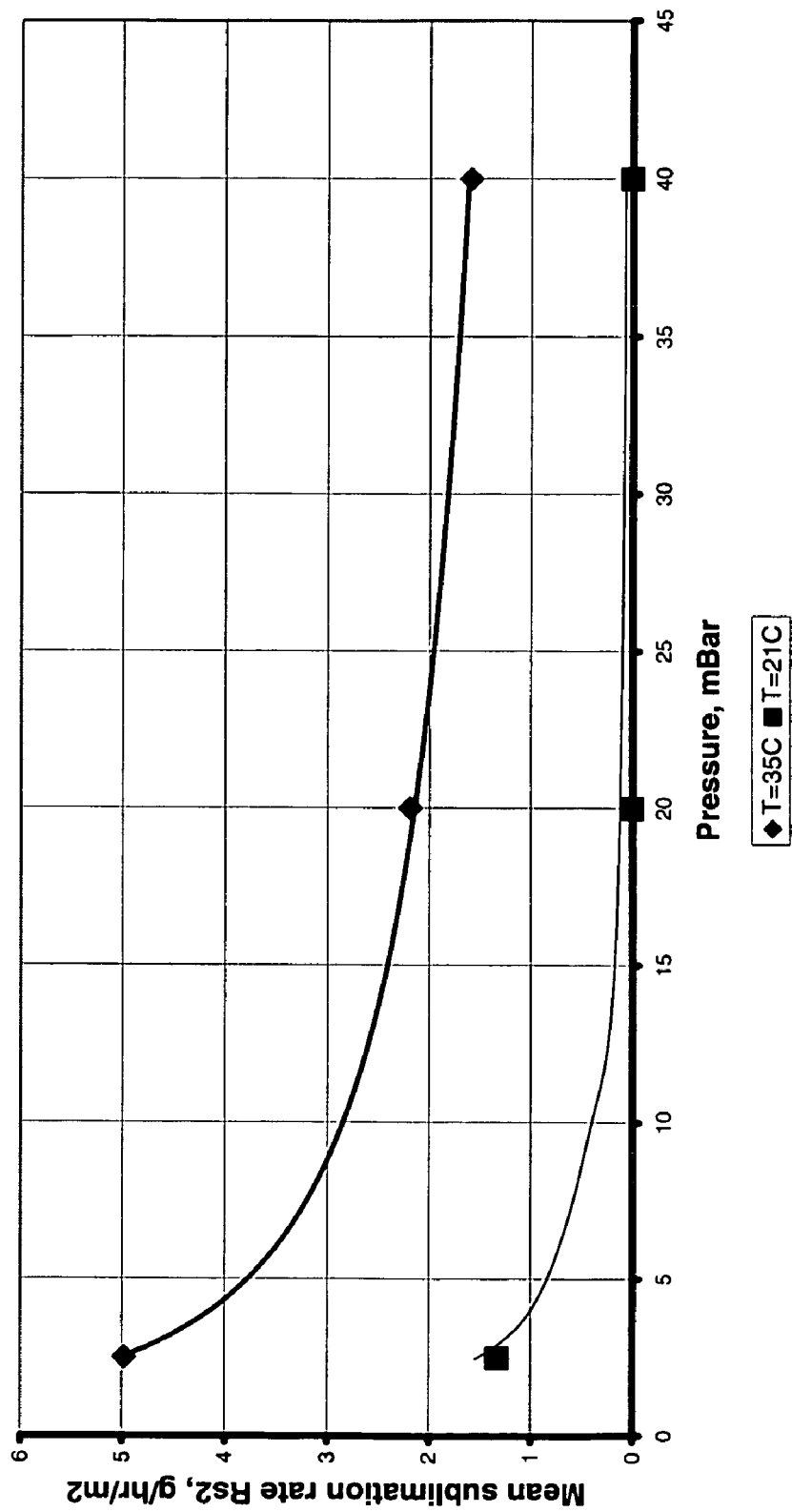
FIG. 2 shows the effect of pressure and temperature on solid rasagiline base sublimation rate.
Figure 3:
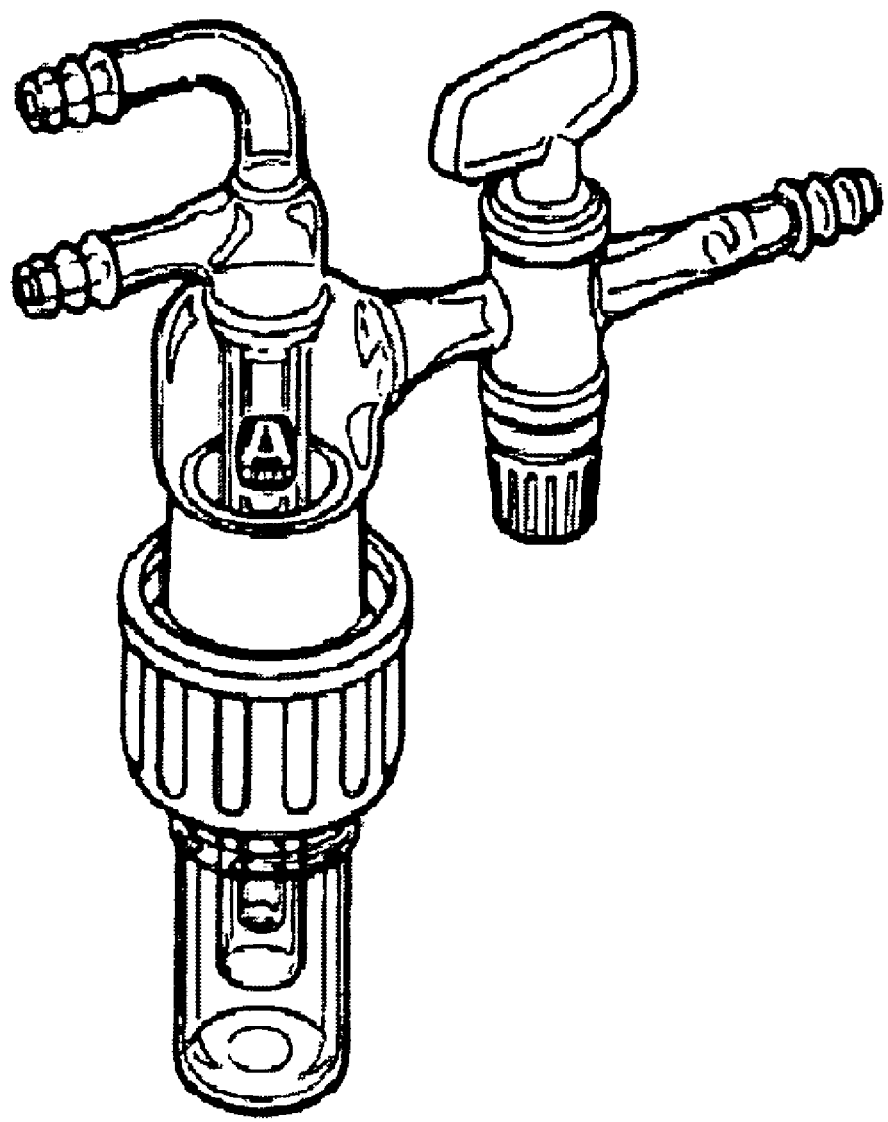
FIG. 3 shows an exemplary apparatus which may be used for sublimation.

Effects of vacuum and temperature on sublimation rate of rasagiline base and racemic PAI base are represented graphically on FIG. 1 and FIG. 2.

FIG. 1 demonstrates that at high vacuum (pressure less than 3 mbar) and elevated temperatures (60° C. and higher), high sublimation rate was observed.

FIG. 2 demonstrates that at moderate vacuum (pressure higher than 20 mbar) and low temperatures (less than 22° C.), zero sublimation rate was observed.

CONCLUSIONS

Sublimation provides crystalline material with higher particle size and better color purity (colorless) than the conventional crystallization process.

High vacuum (pressure less than 3 mbar) and elevated temperature (60° C. and higher) are suitable as conditions for purification of rasagiline and racemic PAI bases by sublimation.

Set 3

Process for Purifying Liquid Rasagiline Base

Liquid Rasagiline base (oil) discussed in the previous patents and applications, e.g. as a process intermediate, is not pure enough to be used as Active Pharmaceutical Ingredient (API). Usually liquid Rasagiline base (oil) has low Rasagiline assay (<98%) and contains high level of impurities, including organic volatile impurities (OVIs), 1-Aminoindan, S-isomer, etc.

Liquid Rasagiline base of acceptable purity would be useful as an API in a drug product for its storage, transport, and mixing properties.

The procedures described in the Examples below disclose methods of purification and stabilization of liquid drug substance of Rasagiline base.

Liquid Rasagiline base of acceptable purity (assay>98%) can be obtained by melting pure Rasagiline base having low melting point (38-40° C.) and addition of small amount of additive (pharmaceutically acceptable solvent) to the melt. The resulting liquid product does not solidify at lower temperatures (2-25° C.) allowing its storage in a refrigerator.

The solvents that can be used as the additive are pharmaceutically acceptable liquids miscible with Rasagiline base melt, including ethanol, PEG, vegetable oil, glycerol, etc. The mount of the additive may be between 0.5 and 50%.

Preservatives and antioxidants as BHT, Tocopherol, carotenoids, etc. can also be added to the liquid product to improve its chemical stability.

Example 25

Preparation of Stabile Liquid Rasagiline Base Of Pharmaceutical Purity by Sublimation Four grams (gm) of Rasagiline base is introduced into the sublimation reservoir of sublimation apparatus. The apparatus then is closed and circulation of coolant (ice water) is started. The vacuum then is built to a pressure of 2-3 mbar and the reservoir is introduced into thermostatic water bath. The water bath is heated to 60° C., the solid is sublimed and until 80-90% of material is sublimed and forms a solid on the sublimation head.

After completion of sublimation the heating is stopped, atmospheric pressure in the apparatus is build up and the apparatus is opened.

The sublimation head with the sublime solid is transferred into a glass container and temperature of the circulation coolant is raised to 50° C. causing melting of the sublimed Rasagiline base into liquid.

3.2 g of liquid Rasagiline base is obtained and a sample is analyzed for Assay and purity by HPLC.

Subsequently, 0.16 g (5.0% wt.) of USP grade Ethanol is added to the liquid product and mixed. The liquid is de-aerated with inert gas (Nitrogen) and sealed.

Resulting liquid is cooled to room temperature and stored in refrigerator at ±5° C. for 1 week with no signs of solidification or crystals precipitation.

Example 26

Preparation of Stabile Liquid Rasagiline Base Of Pharmaceutical Purity by Distillation Crude Rasagiline base (10 g) is charged into bottom flask of glass high-vacuum distillation unit.

The flask is heated by oil bath and condenser and distillate receiver are chilled by circulation of water from water bath.

Vacuum (1-2 mmHg) is build up. Then the bottom flask is heated and temperature of circulating water is maintained between +1 and +10° C. Rasagiline base begins to distill under vacuum.

Low-boiling head fraction is collected and discarded then temperature of the circulating water is raised to +40° C. preventing the distillate crystallization.

After completion of the distillation of main fraction the heating of the bottom flask is stopped and atmospheric pressure in the system is build-up with inert gas (Nitrogen).

Liquid distillate is sampled for and analyzed for Assay and purity by HPLC.

The hot distillate (8.5 g) is then transferred to the glass bottle with 0.39 g PEG 400 (4.5% wt.) and mixed. The liquid is de-aerated with inert gas (Nitrogen) and sealed.

Resulting liquid is cooled to room temperature and stored in refrigerator at +5° C. for 1 week with no signs of solidification or crystals precipitation.

What is claimed is:

1. A process for purification of N-propargyl-1-aminoindan comprising:
    a) introducing an amount of solid N-propargyl-1-aminoindan into a sublimation reservoir of a sublimation apparatus;
    b) cooling the sublimation reservoir and building up a vacuum in the sublimation reservoir;
    c) heating the sublimation reservoir so as to sublime the solid N-propargyl-1-aminoindan and to recrystallize the N-propargyl-1-aminoindan from the sublimed form; and
    d) recovering the recrystallized N-propargyl-1-aminoindan, thereby purifying the N-propargyl-1-aminoindan.

2. The process of claim 1, wherein the N-propargyl-1-aminoindan is R(+)-N-propargyl-1-aminoindan.

3. The process of claim 1, wherein the N-propargyl-1-aminoindan is racemic N-propargyl-1-aminoindan.

4. The process of claim 1, wherein the sublimation reservoir is heated to between 35° C. to 200° C.

5. The process of claim 1, wherein the sublimation reservoir is heated to 60° C.

6. The process of claim 1, wherein the pressure at the sublimation reservoir is 20 mbar or lower.

7. The process of claim 1, wherein the pressure at the sublimation reservoir is 3 mbar or lower.

8. The process of claim 1, wherein the recrystallized N-propargyl-1-aminoindan is of enhanced purity relative to the N-propargyl-1-aminoindan prior to sublimation.

9. The process of claim 1, wherein the recrystallized N-propargyl-1-aminoindan is colorless relative to the N-propargyl-1-aminoindan prior to sublimation.

10. The process of claim 1, where in the recrystallized R(+)-N-propargyl-1-aminoindan has crystals of greater average size than the crystalline R(+)-N-propargyl-1-aminoindan prior to sublimation.

11. A process for preparing a pharmaceutical composition comprising crystalline N-propargyl-1-aminoindan and a pharmaceutically acceptable carrier, comprising
    combining the recrystallized N-propargyl-1-aminoindan recovered in step d) of the process of claim 1 with the pharmaceutically acceptable carrier, thereby preparing the pharmaceutical composition.

12. A process for producing an isolated liquid N-propargyl-1-aminoindan containing greater than 98% R(+)-N-propargyl-1-aminoindan comprising:
    a) introducing an amount of N-propargyl-1-aminoindan base into a sublimation reservoir of a sublimation apparatus;
    b) cooling the sublimation reservoir and building up a vacuum in the sublimation reservoir;
    c) heating the sublimation reservoir so as to sublime the N-propargyl-1-aminoindan and to recrystallize the N-propargyl-1-aminoindan from the sublimed form;
    d) collecting the recrystallized N-propargyl-1-aminoindan from the sublimation head and heat the collected sublimed Rasagiline base into liquid; and
    e) mixing the liquid Rasagiline base with a solvent.

13. The process of claim 12, wherein in step a) the sublimation reservoir is heated to between 35° C. to 200° C.

14. The process of claim 12, wherein in step b) the pressure at the sublimation reservoir is 20 mbar or lower.

15. The process of claim 12, wherein the sublimation reservoir is heated to 60° C.

16. The process of claim 13, wherein the sublimation reservoir is heated to 60° C.

17. The process of claim 14, wherein the pressure at the sublimation reservoir is 3 mbar or lower.

18. The process of claim 12, wherein in step e) the solvent is a pharmaceutically acceptable solvent.

19. The process of claim 18, wherein the pharmaceutically acceptable solvent is ethanol, PEG, vegetable oil, or glycerol.

20. The process of claim 19, wherein the solvent is ethanol.

* * * * *